(12) United States Patent
Ye et al.

(10) Patent No.: US 11,192,155 B2
(45) Date of Patent: Dec. 7, 2021

(54) PHAGE AND USE THEREOF IN SOIL REMEDIATION

(71) Applicant: Institute of Soil Science, Chinese Academy of Sciences, Nanjing (CN)

(72) Inventors: Mao Ye, Nanjing (CN); Yuanchao Zhao, Nanjing (CN); Mingming Sun, Nanjing (CN); Zhongyun Zhang, Nanjing (CN); Dan Huang, Nanjing (CN); Yongrong Bian, Nanjing (CN); Feng Hu, Nanjing (CN); Xin Jiang, Nanjing (CN)

(73) Assignee: INSTITUTE OF SOIL SCIENCE, CHINESE ACADEMY OF SCIENCES, Nanjing (CN)

( * ) Notice: Subject to any disclaimer, the term of this patent is extended or adjusted under 35 U.S.C. 154(b) by 126 days.

(21) Appl. No.: 16/547,051

(22) Filed: Aug. 21, 2019

(65) Prior Publication Data
US 2020/0061684 A1 Feb. 27, 2020

(30) Foreign Application Priority Data
Aug. 22, 2018 (CN) .......................... 201810959953.9

(51) Int. Cl.
*B09C 1/10* (2006.01)
*C12N 7/00* (2006.01)

(52) U.S. Cl.
CPC ............... *B09C 1/10* (2013.01); *C12N 7/00* (2013.01); *C12N 2795/00011* (2013.01)

(58) Field of Classification Search
CPC .......... C12N 2795/00011; C12N 2795/00021; C12N 2795/00032; C12N 7/00; A61K 2300/00; A61K 38/164; A61K 48/00; C11D 3/381; Y02E 50/10; A61P 31/04; A01N 63/40; B09C 1/10
See application file for complete search history.

(56) References Cited

FOREIGN PATENT DOCUMENTS

| CN | 102199576 | 9/2011 |
| CN | 106754745 | 5/2017 |
| CN | 106929481 | 7/2017 |
| CN | 108070572 | 5/2018 |

OTHER PUBLICATIONS

Lanning et al. Journal of General Microbiology (1982), vol. 128, pp. 2063-2071.*
First Office Action dated Apr. 18, 2019 for Chinese Patent Application 201810959953.9.
Notification to Grant Patent dated May 9, 2019 for Chinese Patent Application 201810959953.9.

* cited by examiner

*Primary Examiner* — Bao Q Li
(74) *Attorney, Agent, or Firm* — Lei Fang; Smith Tempel Blaha LLC

(57) ABSTRACT

A phage and use thereof in soil remediation are disclosed. The phage φYSZPK has been deposited at the China Center for Type Culture Collection on Aug. 1, 2018 under Accession No. CCTCC M 2018516, and its taxonomic designation is *Pseudomonas aeruginosa* and *Klebsiella* phage φYSZPK. Biochar and the screened phage are combined and returned into contaminated soil to synergistically control and deeply track and inactivate transmission and spread of antibiotic resistance pathogenic bacteria and resistance genes in a soil-vegetable system. The combination of the biochar and the phage φYSZPK not only clearly improves the functional stability of microbial community in the soil-vegetable system, but also significantly alleviates the dissemination of the antibiotic resistance pathogenic bacteria in the soil-vegetable system to prevent secondary pollution, thereby providing a new solution for biological remediation and control of farmland soil contaminated by antibiotic resistance pathogenic bacteria in China.

6 Claims, 3 Drawing Sheets

PHAGE AND USE THEREOF IN SOIL REMEDIATION

CROSS-REFERENCE TO RELATED APPLICATIONS

This U.S. application claims benefit and priority to Chinese Application No. 201810959953.9 filed on Aug. 22, 2018, which is incorporated by reference herein in its entirety.

FIELD OF THE INVENTION

The present invention belongs to the technical field of remediation of compound contaminated soil of multiple antibiotic resistance pathogenic bacteria and related resistance genes thereof, and particularly relates to a phage φYSZPK and use thereof in controlling and inactivating antibiotic resistance pathogenic bacteria in a soil-vegetable system.

DESCRIPTION OF RELATED ART

In recent years, due to the abuse of antibiotic veterinary drugs, the defect of a safe treatment technology for livestock and poultry manure, and the lack of environmental management, in China and many countries around the world, farmland soil-vegetable systems around suburban livestock farming plants often become high-risk hotspot "sources" and "sinks" for residues and breeding of antibiotic resistance bacteria (ARB) and antibiotic resistance genes (ARGs). Especially, under the promotion of horizontal transfer or vertical transduction of a large number of movable gene elements (plasmids, integrons, and transposons) in an environment, the risk of spread and transmission of some zoonotic antibiotic resistance pathogenic bacteria is greatly increased, and furthermore, it causes a very serious potential threat to human health and ecological safety. Therefore, it is very necessary and urgent to develop the technical invention of biochar control and phage therapy for targetedly inactivating antibiotic resistance pathogenic bacteria in soil-vegetable systems.

Biochar is an environment-friendly functional material produced by burning plants (crops) and wastes thereof at a high temperature under partial or complete anoxic conditions, and the biochar has multiple pores, a large specific surface area and a strong adsorption capacity, and can provide indigenous microorganism implantation. Researches show that, in the farmland soil around livestock and poultry farms and covering soil around medical waste treatment plants and landfills, the addition of the biochar can efficiently, broadly and synergistically control the transmission path, transmission frequency and transmission distance of multiple ARB and ARGs in soil-plant systems, the risk of spread of ARB and ARGs in the environment is effectively reduced under the obstruction, adsorption and reduction promotion effects of the biochar, and furthermore, the application of the biochar is favorable for preserving the fertility of soil, improving the crop quality and increasing the crop yield.

Bacteriophages (abbreviated as phages) are a kind of organisms which survive by exclusively preying on living host bacteria, and are widely distributed in soil, water, air, and even human and animal body surfaces or intestinal tracts. It is estimated that the total quantity of the phages reaches the order of magnitudes of $10^{31}$. Phage therapy refers to a remediation mode of separating, screening, purifying and enriching the phages of host bacteria, then screening polyvalent phages with high titer, short lysis period and strong stress resistance, then adding specific phage bacterial liquid to a contaminated soil-plant system, and directionally infecting and inactivating pathogenic bacteria.

Through relevant literature review and patent search, publication and acceptance of biochar and phage therapy for the biological remediation technology for compound high-abundance antibiotic resistance pathogenic bacterium and resistance gene contaminated soil-vegetable systems are not found. The existing methods most similar to the present invention are related applications of biochar for adsorption and removal of Escherichia coli alone or in combination with bacterial agents and control of soil-borne diseases, and phage therapy for specific inactivation of Pseudomonas aeruginosa or prevention of bacterial wilt of crops. Chinese patent applications CN201310256154.2, CN201710345239.6, CN201710558388.0, CN201710089442.1, CN201580008049.4, and CN201510008569.7 respectively relate to absorption of Escherichia coli in water by modified biochar, removal of organic/inorganic contaminants in soil groundwater systems by combination of biochar and fly ash, control of watermelon fusarium wilt by combination of biochar and biological agents, inactivation of Pseudomonas aeruginosa/Escherichia coli by attack of high-specificity phages, and control of Ralstonia solanacearum of tobacco bacterial wilt by phage therapy. At present, the existing main research method is to singly use the biochar or the phage therapy to adsorb and remove pathogenic bacteria to prevent diseases of plants/crops. However, there is almost no remediation technology for combination of the biochar and the phage therapy to reduce the compound contamination of ARB and ARGs in soil-vegetable systems. The patent application CN201310256154.2 provides an application of aluminum modified straw biochar in removal of Escherichia coli in water. According to the invention, the biochar and 0.6 mol/L molten aluminum are mixed and added to water, and after a reaction reaches saturation, the biochar is filtered off and Escherichia coli is inactivated by high-temperature calcination. The patent application N201710558388.0 provides a preparation method of biochar and microbial agents for controlling watermelon fusarium wilt. According to the invention, the biochar, watermelon fusarium wilt bio-control bacteria, attapulgite, calcium superphosphate and the like are mixed and granulated, and the compound material can effectively prevent the watermelon fusarium wilt and increase the crop yield. The patent application N201710558388.0 provides a remediation method for treating contaminated soil and groundwater by fly ash and biochar. According to the invention, a mixture of the fly ash and the biochar is used for performing comprehensive soil remediation treatment on top soil, deep soil and groundwater of industrial and agricultural contaminated land, and representing removal effects according to the growth conditions of indigenous microbial community and the varieties and distribution characteristics of organic/inorganic contaminants. The patent applications N201580008049.3 and CN201580008049.4 respectively provide a method for treating Pseudomonas aeruginosa/colon bacillus infection by a phage combined agent. According to the inventions, specific pathogenic bacteria are used as host bacteria to screen a large amount of phages in environmental samples, a high-activity phage combination is selected as a raw material for preparation of the agent, and "many-to-one" efficient inactivation can be performed for Pseudomonas aeruginosa/colon bacillus. The patent application CN201510008569.7 provides a technical method for controlling tobacco bacterial wilt by phage therapy. The method mainly uses a sterile injector to inject a prepared phage suspension to tobacco stems and uses mineral oil to cover the outer side.

These methods all indicate that both the biochar and the phage can control and even inactivate pathogenic bacteria, and can simultaneously prevent diseases of crops, but generally lack the overall remediation effect on synergistic removal of ARB and ARGs in soil-crop (vegetable) systems. Furthermore, the prior art do not involve the introduction for inactivation of pathogenic bacteria carrying antibiotic resistance genes in soil-vegetable systems by combination of the biochar and the phage.

The existing technologies have the following main defects: In most of the existing patent researches, the biochar is used as an adsorbing material to remove organic contaminants, inorganic contaminants, heavy metal contaminants and the like in the contaminated soil, or the biochar is used for improving soil properties, adjusting the soil fertility and increasing the crop quality and yield. However, there are fewer researches on broad-spectrum adsorption and removal of antibiotic resistance pathogenic bacteria in soil. Furthermore, the related ecological risk assessment of the functional stability and diversity of microbial community in soil-vegetable systems after inoculation is relatively scarce. In most of the existing phage therapy applications, phages with strong selectivity and high specificity are used as primary materials, biological control technologies for simultaneous inactivation of the compound contamination of multiple antibiotic resistance pathogenic bacteria in soil-vegetable systems are lacking, and furthermore, the related ecological risk assessment of the functional stability and diversity of microbial community in soil-vegetable systems after inoculation has received little attention.

The main reasons for the defects are as follows: In recent years, the academic community has gradually recognized that soil-vegetable systems are "sources" and "sinks" for accumulation of multiple antibiotic resistance bacteria and resistance genes, and this type of novel resistance pathogenic bacteria and genes will seriously threaten the human health and ecological environment safety through the transfer action of food chains. Most of the existing remediation researches are the inactivation remediation of *Escherichia coli/Pseudomonas aeruginosa* in water or the researches of *Ralstonia solanacearum* causing bacterial wilt of crops, attention to bacteria with high pathogenic risk (such as *Klebsiella pneumoniae* and *Pseudomonas aeruginosa*) in soil-vegetables is lacking, and less attention is paid to the contamination of high-abundance compound resistance pathogenic bacteria and resistance genes in soil-vegetable systems. Therefore, it is urgent to carry out the research and development of a bio-targeted inactivation technology for specifically controlling and eliminating the risk of accumulation of ARB and ARGs in soil-vegetable systems.

SUMMARY OF THE INVENTION

Technical Problem

Aiming at the defects of the prior art, the present invention provides a phage and use thereof in soil remediation. The present invention adopts a remediation method of adding biochar and specific phage bacterial liquid to a contaminated soil-plant system for control and targeted inactivation of the compound contamination of resistance pathogenic bacteria in a contaminated soil system to synergistically remove resistance genes. After the remediation, the functional diversity and stability of a soil ecological environment are significantly restored. The present invention is a biological remediation technology with environmental friendliness.

Technical Solution

A phage φYSZPK has been deposited at the China Center for Type Culture Collection on Aug. 1, 2018 under Accession No. CCTCC M 2018516, and its taxonomic designation is *Pseudomoims aeruginosa* and *Klebsiella* phage φYSZPK. They are deposited at China Center for Type Culture Collection, Wuhan University, Luojia Hills, Wuchang, Wuhan, Hubei Province.

Use of said phage φYSZPK in simultaneous lysis of *Klebsiella pneumoniae* and *Pseudomonas aeruginosa* PAO1.

Use of said phage φYSZPK in control and inactivation of antibiotic resistance pathogenic bacteria in a soil-vegetable system.

Use of said phage φYSZPK in combination with biochar in control and inactivation of antibiotic resistance pathogenic bacteria in a soil-vegetable system.

The biochar is produced by burning wheat straw as a raw material at a high temperature of 450° C., and basic physical and chemical properties are as follows: total carbon: 548.4 g/kg, total nitrogen: 13.4 g/kg, C/N: 33.6, ash content: 175.5 g/kg, total phosphorus: 2.1 g/kg, total potassium: 10.3 g/kg, and pH: 8.5.

The phage φYSZPK and the biochar are mixed in a mass ratio of 1:1000 and then returned into contaminated soil.

The phage φYSZPK is used for preparing a product for simultaneous lysis of *Klebsiella pneumoniae* and *Pseudomonas aeruginosa* PAO1.

The phage φYSZPK is used for preparing a product for control and inactivation of antibiotic resistance pathogenic bacteria in a soil-vegetable system.

A product for control and inactivation of antibiotic resistance pathogenic bacteria in a soil-vegetable system contains the phage φYSZPK and biochar.

The working principle of the present invention is as follows: 1. the biochar is a kind of environment-friendly material which is more in porosity, high in specific surface area, stable in chemical structure and rich in surface functional groups and contains a large number of elements such as C, N, P, Ca, and Mg; 2. the biochar can adsorb and control contaminants (including pesticide residues, organic solvents, heavy metal ions, polycyclic aromatic hydrocarbons, and the like) in soil or water so as to reduce the environmental risk, and furthermore, the biochar can be applied into the soil to achieve the effects of preserving moisture and fertility, improving physical and chemical properties of the soil and increasing the crop yield; 3. phages are a kind of bacterial viruses surviving by specifically infecting host bacteria, and can be divided into lytic phages and lysogenic phages; 4. the lytic phages can recognize the specific binding sites of the surfaces of cell membranes of host bacteria in the environmental migration process and perform paired adsorption, subsequently, the tail sheaths of the phages shrink, the DNA of the nucleic acids is injected into the host bacteria through hollow tails to execute an invasion process, then, the DNA of the phages utilizes the nucleic acid base pairs and energy substances in the host to rapidly complete its own nucleic acid replication and protein synthesis, a large number of progeny phages are assembled and proliferated in the bacteria, and cell wall lytic enzymes are released, thereby causing the host bacteria to rupture and die and destroying the internal structure of the bacteria so as to finally complete lysis and release processes; 5. a lytic phage with high titer, short lysis period and strong stress resistance is selected by simulation according to in-situ contaminated soil environmental conditions (temperature, pH, ion concentration, and the like) so as to be used as a preferred strain for phage therapy, the lytic phage will preferentially "prey on" pathogenic bacteria with higher specificity in the environment, after this type of pathogenic bacteria are reduced to a certain level, the lytic phage will attack host bacteria with weaker specificity and maintain its survival state at a certain level, and furthermore, secondary pollution of the pathogenic bacteria can be prevented; 6. there are ten or dozens of phages around each bacterium in the soil environment, and some phages will be transferred into vegetables by means of plant root penetration and leaf surface transpiration to simultaneously track and inactivate resistance pathogenic bacteria in the vegetables, thereby controlling the transmission and spread of the resistance pathogenic bacteria and indirectly preventing the human health from being affected due to food chain transfer action; 7. the selected phages are derived from the soil and finally returned to the soil without any modification, and thus are environmentally friendly; 8. the ecological risk after application of the phage therapy is evaluated to ensure the ecological functional diversity and stability of microorganisms.

Advantageous Effect

The invention relates to a method for controlling and inactivating compound high-abundance resistance pathogenic bacteria in soil-vegetable systems by combination of biochar and phage therapy, and provides a rapid remediation technology. The present invention has the following main advantages: 1. The biochar can broadly control compound resistance pathogenic bacteria and resistance genes in the contaminated soil; 2. The application of the biochar is favorable for preserving moisture and fertility of soil, improving the crop quality and increasing the crop yield; 3. The phage can realize targeted inactivation of resistance pathogenic bacteria in the contaminated soil, and can simultaneously reduce the abundance of related resistance genes; 4. The biochar and the phage are low in preparation cost, convenient in storage and transport and simple and convenient in use and operation, can realize broad spectrum control and accurate targeted inactivation, can prevent secondary pollution after remediation, and are easy for popularization; 5. The combination of the biochar and the phage can clearly improve the ecological functional diversity and stability of microorganisms in soil, and is environmentally friendly. The method has broad application prospects for remediation of compound high-concentration antibiotic resistance pathogenic bacterium contaminated soil around a large number of livestock and poultry farms in China.

DETAILED DESCRIPTION OF THE INVENTION

Figure 1:
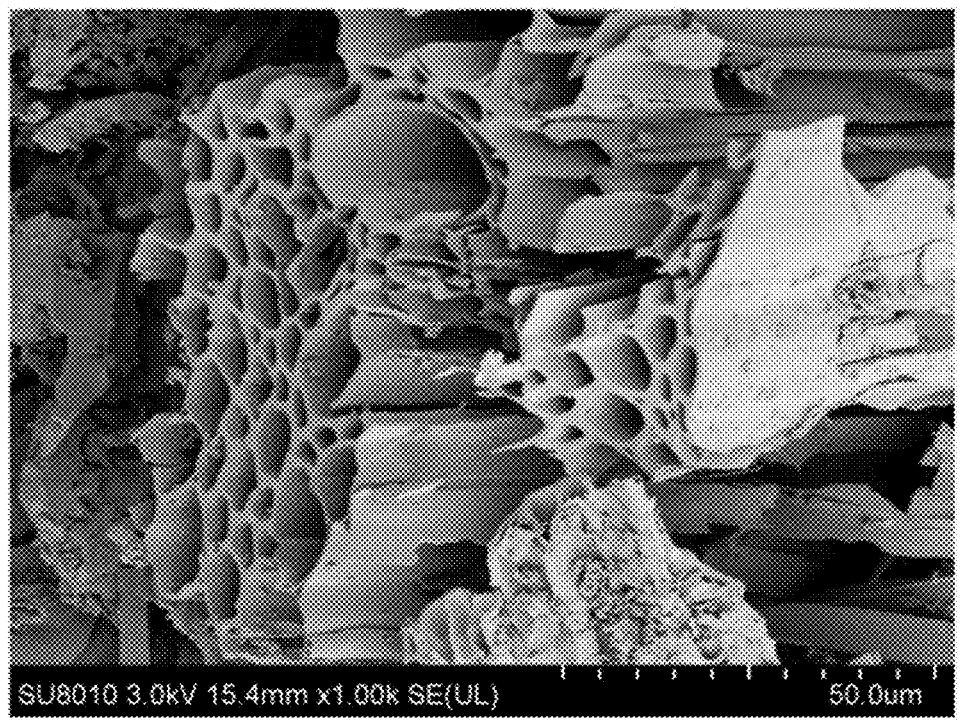
FIG. 1 is a scanning electron micrograph of biochar.
Figure 2:
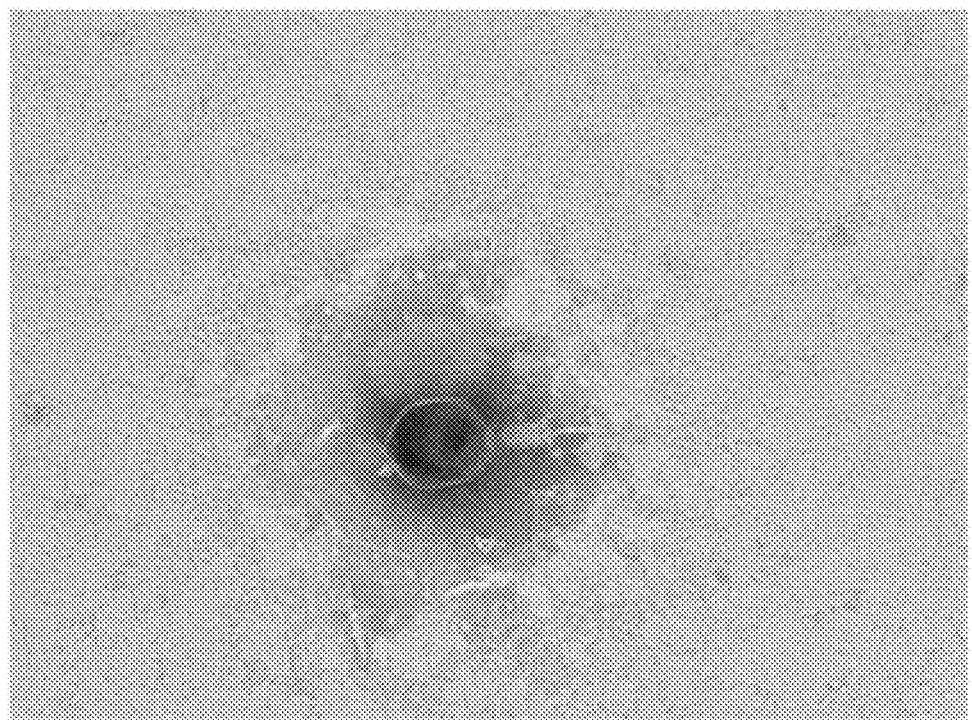
FIG. 2 is a transmission electron micrograph of a phage φYSZPK.
Figure 3:
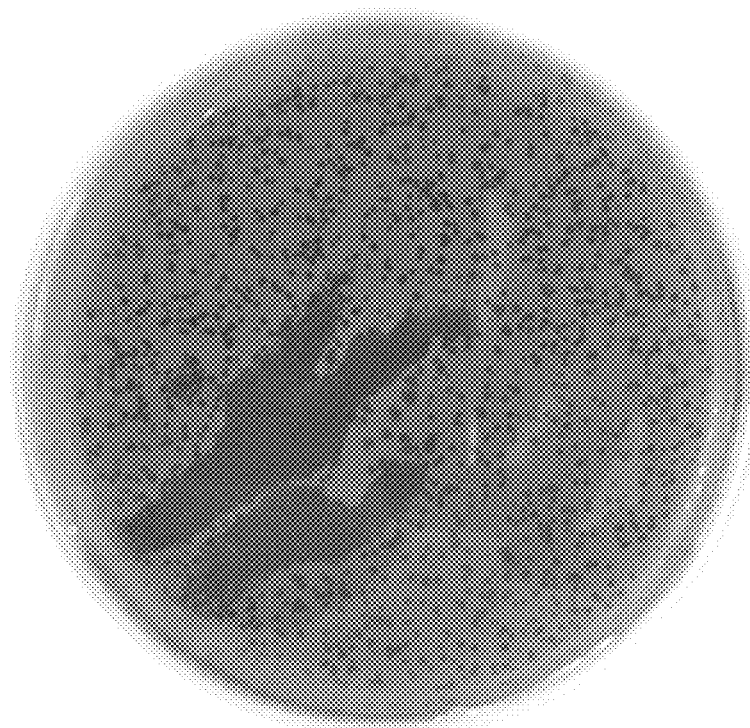
FIG. 3 is a flat graph of forms of phage plaques of the phage φYSZPK.
Figure 4:
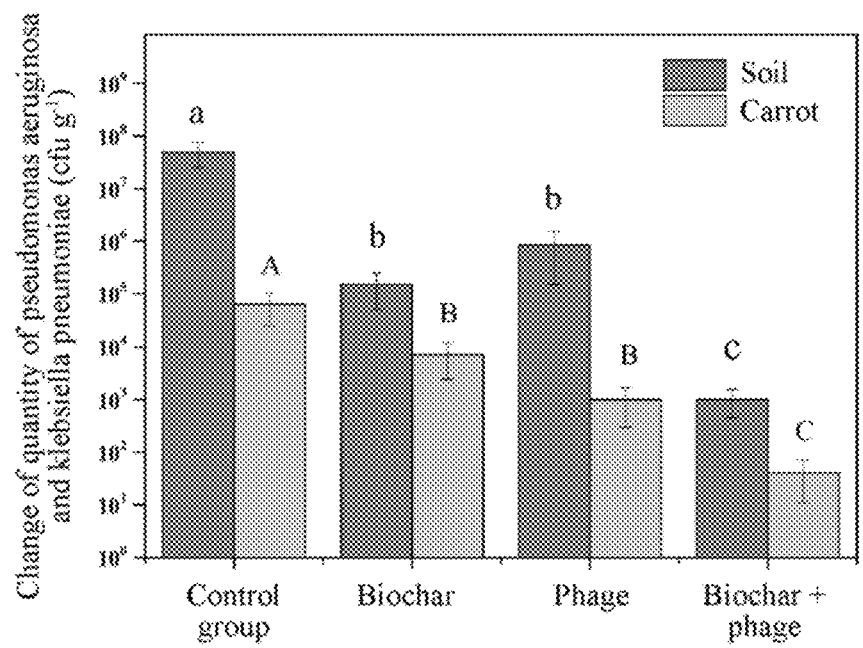
FIG. 4 is a verification diagram of control and inactivation effects on *Klebsiella pneumoniae* and *Pseudomonas aeruginosa* in a contaminated soil-vegetable system of a manure accumulation place of the Hengliang dairy farm in Nanjing, Jiangsu Province, when carrots are planted on contaminated soil by using the technical solution of the present invention.
Figure 5:
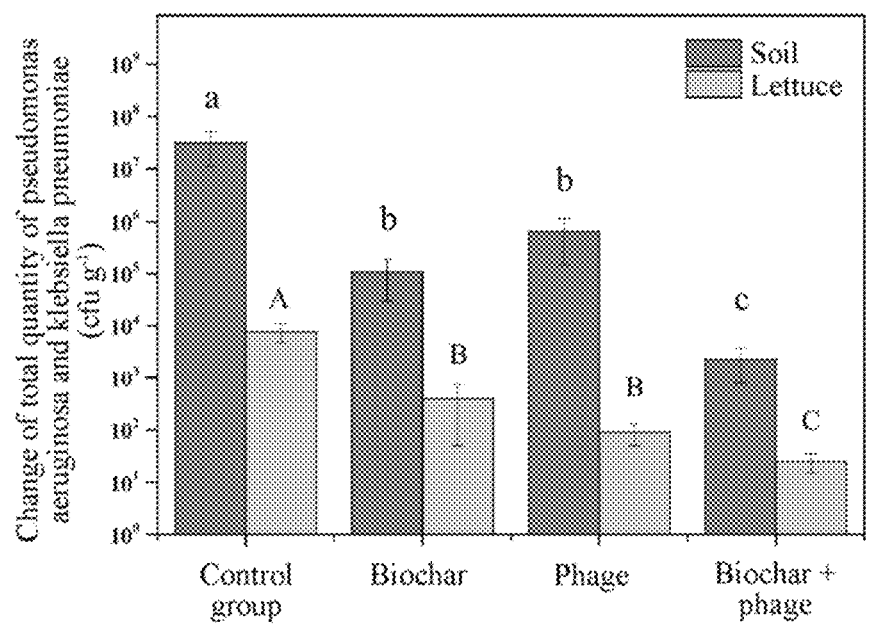
FIG. 5 is a verification diagram of control and inactivation effects on *Klebsiella pneumoniae* and *Pseudomonas aeruginosa* in a contaminated soil-vegetable system of the manure accumulation place of the Hengliang dairy farm in Nanjing, Jiangsu Province, when pod peppers are planted on the contaminated soil by using the technical solution of the present invention.
Figure 6:
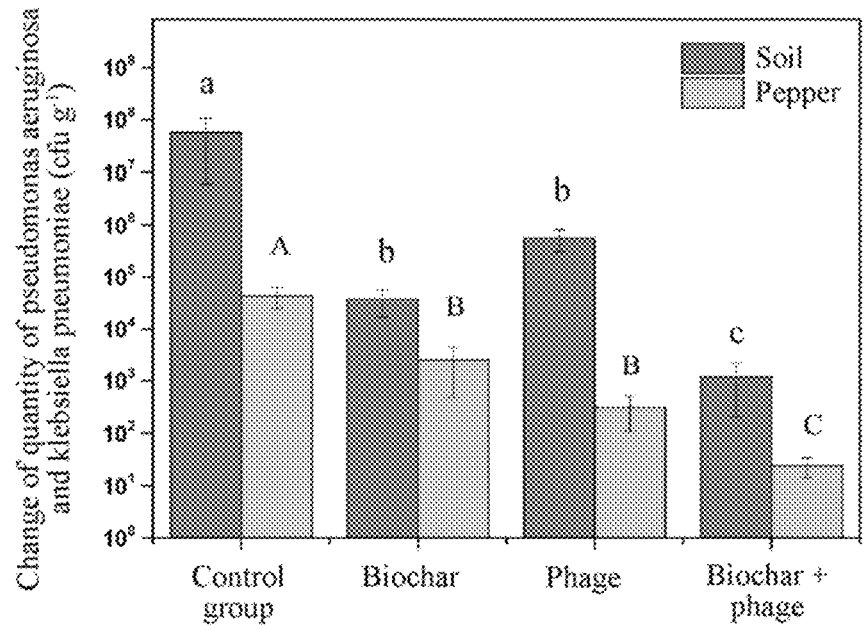
FIG. 6 is a verification diagram of control and inactivation effects on *Klebsiella pneumoniae* and *Pseudomonas aeruginosa* in a contaminated soil-vegetable system of the manure accumulation place of the Hengliang dairy farm in Nanjing, Jiangsu Province, when lettuces are planted on the contaminated soil by using the technical solution of the present invention.

The following specific implementation manners do not limit the technical solution of the present invention in any form. Any technical solution obtained by means of equivalent replacement or equivalent transformation falls within the protection scope of the present invention.

Biochar B is produced by burning wheat straw as a raw material at the high temperature of 450° C., and the pH of the biochar B is alkaline.

The Accession No. of the phage φYSZPK is CCTCC M 2018516. An electron micrograph shows that the phage φYSZPK has an elliptical head and a shrinkable tail sheath, and has a head long diameter of about 110 nm, a transverse diameter of about 80 nm, and a tail length of about 120 nm, and phage plaques on a culture dish are transparent in the middle, have no halo around, and have a diameter of about 2-3 mm.

The resistance gene ampC refers to a resistance gene carrying chloramphenicol on plasmids in *Pseudomonas aeruginosa* PAO1 cells.

The resistance gene tetW refers to a resistance gene carrying tetracycline antibiotics on plasmids in *Klebsiella pneumoniae* cells.

The potting soil is obtained by respectively adding the same abundance of pathogenic bacteria (*Pseudomonas aeruginosa* PAO1 and *Klebsiella pneumoniae*) to collected raw soil.

Example 1

Test potting soil was collected from contaminated soil around a manure accumulation pool of the Hengliang dairy farm in Nanjing, Jiangsu Province. Basic physical and chemical properties of the soil were as follows: sand grain: 23.8%, soil grain: 45.4%, clay grain: 31.8%, pH: 7.7, total nitrogen: 1.7 g·kg$^{-1}$, water-soluble nitrogen: 1.7 g·kg$^{-1}$, total phosphorus: 1.3 g·kg$^{-1}$, total potassium: 17.5 g·kg$^{-1}$, and CEC: 19.4 cmol·kg$^{-1}$.

5 g of fresh soil samples were taken and added to 50 mL of sterile water, shake culture was performed for 5 h at 28° C. and 150 rpm, centrifugation was performed for 5 min at 10000 rpm, the supernatant liquid was sterilized by a 0.22 μm filter membrane, 9 mL of filtrate and 1 mL of a suspension of *Pseudomonas aeruginosa* PAO1 growing to a logarithmic phase were taken and added to 40 mL of LB liquid culture medium, calcium chloride solids were added until the final concentration of the solution was 1 mmol·L$^{-1}$, shake culture was performed for 12 h at 30° C. and 150 rpm, the obtained culture solution was centrifuged for 5 min at 10000 rpm, and then, the centrifuged culture solution was sterilized by a 0.22 μm filter membrane to obtain a phage stock solution; phages were screened and purified by using a double-layer flat plate method, 100 μL of filtrate and 100 μL of *Klebsiella pneumoniae* suspension were taken and mixed uniformly, the mixture was allowed to stand for 15 min at room temperature, the mixture was added to 3 mL of 0.7% LB agar culture medium and horizontally poured on an LB solid flat plate after uniform mixing, culture was performed for 10-12 h at 30° C., phage plaques were observed, after the phage plaques occurred, a single phage plaque with clear and transparent edges was taken in LB liquid containing host bacteria so as to be purified, and the purified product was refrigerated at 4° C.; and 600 pt of preserved phage stock solution was taken and added to 99 mL of LB liquid culture medium together with 200 mL of PAO1 and 200 pt of *Klebsiella pneumoniae* mixed suspension respectively, then, calcium chloride solids were added until the final concentration was 1 mmol·L$^{-1}$, shake culture was performed for 96 h at 37° C. and 150 rpm, samples were taken every 8 h, the phage obtained by centrifugal filtration and PAO1 were poured into a double-layer flat plate to be verified, phage plaques were observed, if phage plaques occurred, it was proved that the directed evolution was successful, a polyvalent phage φYSZPK was obtained, a single clear and transparent phage plaque was selected and enriched and mixed with 50% glycerol in a volume ratio of 1:1, and the mixture was preserved at low temperature of −80° C. for later use.

Wheat straw was used as a raw material for preparation of the biochar. 10 kg of wheat straw was weighed and put into a pulverizer and then preliminarily pulverized, the pulverized straw was sieved, 2 kg of sieved wheat straw with 100 meshes was weighed and put into a ceramic crucible, the wheat straw was carbonized for 8 h at the high temperature of 450° C. in a muffle furnace, and then, the carbonized wheat straw was taken out, cooled and stored in a dry place for later use. The measured basic physical and chemical properties were as follows: total carbon: 548.4 g/kg, total nitrogen: 13.4 g/kg, C/N: 33.6, ash content: 175.5 g/kg, total phosphorus: 2.1 g/kg, total potassium: 10.3 g/kg, and pH: 8.5.

Example 2

Test potting soil was collected from the contaminated soil around the manure accumulation pool of the Hengliang dairy farm in Nanjing, Jiangsu Province. Planting vegetables were carrots Seoul six-inch (*Daucus* L.), and were derived from Beijing Zhongnong Tianteng Vegetable Seed Company. Basic physical and chemical properties of the soil were as follows: sand grain: 23.8%, soil grain: 45.4%, clay grain: 31.8%, pH: 7.7, total nitrogen: 1.7 g·kg$^{-1}$, water-soluble nitrogen: 1.7 g·kg$^{-1}$, total phosphorus: 1.3 g·kg$^{-1}$, total potassium: 17.5 g·kg$^{-1}$, and CEC: 19.4 cmol·kg$^{-1}$.

Four groups of treatment were set in experiments: (1) control group (CK): 3 carrots were planted per pot (0.5-1 cm of soil was covered on seeds, and the room temperature was 20±2° C.); (2) biochar treatment (B): the biochar (1 g/kg) was applied on the basis of the control group; (3) phage φYSZPK treatment (P): 100 mL of phage φYSZPK with a concentration of 10$^6$ pfu·mL$^{-1}$ was inoculated on the basis of the control group; (4) biochar and phage φYSZPK combined treatment (BP): the biochar (1 g/kg) was applied and 100 mL of the phage φYSZPK with a concentration of 10$^6$ pfu·mL$^{-1}$ was inoculated on the basis of the control group. The soil and carrots were sampled on the site after the 70th day of carrot growth, the measured quantity of *Pseudomonas aeruginosa* PAO1 in the contaminated soil under the four groups of treatment (CK, B, P, and BP) was respectively 5.1×10$^7$ cfu·g$^{-1}$, 1.5×10$^5$ cfu·g$^{-1}$, 8.3×10$^5$ cfu·g$^{-1}$, and 1.2×10$^3$ cfu·g$^{-1}$, and the abundance of the chloramphenicol resistance gene ampC was respectively 1.4×10$^9$ copies·g$^{-1}$, 2.5×10$^6$ copies·g$^1$, 1.3×10$^7$ copies·g$^{-1}$, and 7.8×10$^5$ copies·g$^{-1}$. Under the three groups of treatment (B, P, and BP), compared with the control group, the quantity of *Pseudomonas aeruginosa* PAO1 in the contaminated soil was respectively reduced by 2.3, 1.9, and 4.3 orders of magnitude, and the abundance of the resistance gene ampC was respectively reduced by 2.8, 2.1 and 3.8 orders of magnitude. The measured related quantity of *Klebsiella pneumoniae* in carrot root tubers under the four groups of treatment (CK, B, P, and BP) was respectively 6.2×10$^4$ cfu·g$^1$, 9.2×10$^2$ cfu·g$^1$, 3.3×10$^2$ cfu·g$^1$, and 4.1×10$^1$ cfu·g$^{-1}$, and the abundance of the resistance gene ampC was respectively reduced to 1.6×10$^6$ copies·g$^1$, 1.4×10$^4$ copies·g$^1$, 3.2×10$^3$ copies·g$^1$, and 8.4×10$^2$ copies·g$^1$. In carrot leaves, under the three groups of treatment (B, P, and BP), compared with the control group, the abundance of K12 was respectively reduced by 1.7, 2.3 and 3.2 orders of magnitude, and the abundance of the resistance gene ampC was respectively reduced by 2.1, 2.9 and 3.4 orders of magnitude. The control and inactivation effects of combination of the biochar and the phage on resistance pathogenic bacteria and resistance genes were significantly better than those of single addition of the biochar or inoculation of the phage φYSZPK ($p<0.05$).

The analysis finds that the ecological diversity indexes (AWCD indexes) of microorganisms in the soil environment under the four groups of treatment (CK, B, P, and BP) were respectively 0.61±0.1, 0.64±0.2, 0.58±0.2, and 0.68±0.2, by application of the biochar, compared with the control group, the diversity of microorganisms in soil was increased to a certain degree, by inoculation of the phage φYSZPK, compared with the control group, the diversity of microorganisms in soil was reduced to a certain degree, and the combination of the biochar and the phage φYSZPK for remediation has the most significant promotion effect on the functional diversity and stability of microorganisms in soil ($p<0.05$), indicating that the remediation technology has a significant effect on remediation of the spread of resistance bacteria, and is also favorable for maintaining and improving the ecological functional diversity and stability of microorganisms in soil after remediation.

Example 3

Test potting soil was collected from the contaminated soil around the manure accumulation pool of the Hengliang dairy farm in Nanjing, Jiangsu Province. Planting vegetables were Hongpin No. 1 pod peppers (*Capsicum frutescens* var), and were derived from Qianshu Baihua Seed Industry Company. Basic physical and chemical properties of the soil were as follows: sand grain: 23.8%, soil grain: 45.4%, clay grain: 31.8%, pH: 7.7, total nitrogen: 1.7 g·kg$^{-1}$, water-soluble nitrogen: 1.7 g·kg$^{-1}$, total phosphorus: 1.3 g·kg$^{-1}$, total potassium: 17.5 g·kg$^{-1}$, and CEC: 19.4 cmol·kg$^{-1}$.

Four groups of treatment were set in experiments: (1) control group (CK): 3 pod peppers were planted per pot (0.5-1 cm of soil was covered on seeds, and the room temperature was 25±2° C.); (2) biochar treatment (B): the biochar (1 g/kg) was applied on the basis of the control group; (3) phage φYSZPK treatment (P): 100 mL of phage φYSZPK with a concentration of $10^6$ pfu·mL$^{-1}$ was inoculated on the basis of the control group; (4) biochar and phage φYSZPK combined treatment (BP): the biochar (1 g/kg) was applied and 100 mL of the phage φYSZPK with a concentration of $10^6$ pfu·mL$^{-1}$ was inoculated on the basis of the control group. The soil and pod peppers were sampled on the site after the 70th day of pod pepper growth, the measured contamination concentration of *Pseudomonas aeruginosa* PAO1 in the contaminated soil under the four groups of treatment (CK, B, P, and BP) was respectively $5.2\times 0^7$ cfu·g$^{-1}$, $3.7\times10^4$ cfu·g$^{-1}$, $1.8\times10^5$ cfu·g$^{-1}$, and $2.3\times10^3$ cfu·g$^{-1}$, and the abundance of the chloramphenicol resistance gene ampC was respectively $8.3\times10^8$ copies·g$^{-1}$, $4.8\times10^5$ copies·g$^{-1}$, $3.5\times10^6$ copies·g$^{-1}$, and $4.5\times10^4$ copies·g$^{-1}$. Under the three groups of treatment (B, P, and BP), compared with the control group, the quantity of *Klebsiella pneumoniae* in the contaminated soil was respectively reduced by 3.1, 2.2 and 4.3 orders of magnitude, and the abundance of the resistance gene tetW was respectively reduced by 3.3, 2.2 and 4.5 orders of magnitude. The measured quantity of PAO1 in pod pepper fruits under the four groups of treatment (CK, B, P, and BP) was respectively reduced to $6.3\times10^4$ cfu·g$^{-1}$, $4.8\times10^3$ cfu·g$^{-1}$, $2.2\times10^2$ cfu·g$^{-1}$, and $4.2\times10^1$ cfu·g$^{-1}$, and the abundance of the resistance gene ampC was respectively reduced to $1.8\times10^6$ copies·g$^{-1}$, $8.3\times10^4$ copies·g$^{-1}$, $4.1\times10^3$ copies·g$^{-1}$, and $8.2\times10^2$ copies·g$^{-1}$. Under the three groups of treatment (B, P, and BP), compared with the control group, the quantity of *Klebsiella pneumoniae* in fruits was respectively reduced by 1.1, 2.4 and 3.1 orders of magnitude, and the abundance of the resistance gene tetW was respectively reduced by 1.4, 2.8 and 3.6 orders of magnitude. The control and inactivation effects of combination of the biochar and the phage φYSZPK on resistance pathogenic bacteria and resistance genes were significantly better than those of single addition of the biochar or inoculation of the phage φYSZPK.

The analysis finds that the ecological diversity indexes (AWCD indexes) of microorganisms in the soil environment under the four groups of treatment (CK, B, P, and BP) were respectively $0.51\pm0.1$, $0.55\pm0.2$, $0.47\pm0.2$, and $0.57\pm0.1$, by application of the biochar, compared with the control group, the diversity of microorganisms in soil was increased to a certain degree, by inoculation of the phage φYSZPK, compared with the control group, the diversity of microorganisms in soil was reduced to a certain degree, and the combination of the biochar and the phage φYSZPK for remediation has the most significant promotion effect on the functional diversity and stability of microorganisms in soil ($p<0.05$), indicating that the remediation technology has a significant effect on remediation of the spread of resistance bacteria, and is also favorable for maintaining and improving the ecological functional diversity and stability of microorganisms in soil after remediation.

Example 4

Test potting soil was collected from the contaminated soil around the manure accumulation pool of the Hengliang dairy farm in Nanjing, Jiangsu Province. Planting vegetables were Italian year-round bolting-resistant lettuces (*Lactuca sativa* L), and were derived from Hebei Jinfa Seed Industry Co., Ltd. Basic physical and chemical properties of the soil were as follows: sand grain: 23.8%, soil grain: 45.4%, clay grain: 31.8%, pH: 7.7, total nitrogen: 1.7 g·kg$^{-1}$, water-soluble nitrogen: 1.7 g·kg$^{-1}$, total phosphorus: 1.3 g·kg$^{-1}$, total potassium: 17.5 g·kg$^{-1}$, and CEC: 19.4 cmol·kg$^{-1}$.

Four groups of treatment were set in experiments: (1) control group (CK): 3 lettuces were planted per pot (0.5-1 cm of soil was covered on seeds, and the room temperature was $18\pm2°$ C.); (2) biochar treatment (B): the biochar (1 g/kg) was applied on the basis of the control group; (3) phage φYSZPK treatment (P): 100 mL of phage φYSZPK with a concentration of $10^6$ pfu·mL$^{-1}$ was inoculated on the basis of the control group; (4) biochar and phage φYSZPK combined treatment (BP): the biochar (1 g/kg) was applied and 100 mL of the phage φYSZPK with a concentration of $10^6$ pfumL$^{-1}$ was inoculated on the basis of the control group. The soil and lettuces were sampled on the site after the 60th day of lettuce growth, the measured contamination concentration of *Pseudomonas aeruginosa* PAO1 in the contaminated soil under the four groups of treatment (CK, B, P, and BP) was respectively $2.8\times10^7$ cfu·g$^{-1}$, $1.3\times10^5$ cfu·g$^{-1}$, $5.6\times10^5$ cfu·g$^{-1}$, and $2.4\times10^4$ cfu·g$^1$, and the abundance of the chloramphenicol resistance gene ampC was respectively $1.4\times10^8$ copies·g$^{-1}$, $2.5\times10^5$ copies·g$^{-1}$, $5.3\times10^5$ copies·g$^{-1}$, and $2.8\times10^4$ copies·g$^{-1}$. Under the three groups of treatment (B, P, and BP), compared with the control group, the total quantity of *Klebsiella pneumoniae* in the contaminated soil was respectively reduced by 2.2, 1.6 and 3.1 orders of magnitude, and the abundance of the resistance gene tetW was respectively reduced by 2.8, 2.6 and 3.8 orders of magnitude. The measured quantity of PAO1 in lettuce leaves under the four groups of treatment (CK, B, P, and BP) was respectively: $8.2\times10^3$ cfu·g$^1$, $3.8\times10^2$ cfu·g$^1$, $2.3\times10^2$ cfu·g$^1$, and $3.2\times10^1$ cfu·g$^1$, and the abundance of the resistance gene ampC was respectively $1.6\times10^4$ copies·g$^{-1}$, $8.9\times10^2$ copies·g$^{-1}$, $1.2\times10^2$ copies·g$^{-1}$, and $1.4\times10^1$ copies·g$^1$. Under the three groups of treatment (B, P, and BP), compared with the control group, the quantity of *Klebsiella pneumoniae* in lettuce leaves was respectively reduced by 1.4, 1.9 and 2.5 orders of magnitude, and the abundance of the resistance gene tetW was respectively reduced by 1.3, 2.1 and 3.1 orders of magnitude. The control and inactivation effects of combination of the biochar and the phage φYSZPK on resistance pathogenic bacteria and resistance genes were significantly better than those of single addition of the biochar or inoculation of the phage φYSZPK.

The analysis finds that the ecological diversity indexes (AWCD indexes) of microorganisms in the soil environment under the four groups of treatment (CK, B, P, and BP) were respectively $0.64\pm0.1$, $0.70\pm0.2$, $0.61\pm0.1$, and $0.75\pm0.2$, by application of the biochar, compared with the control group, the diversity of microorganisms in soil was increased to a certain degree, by inoculation of the phage φYSZPK, compared with the control group, the diversity of microorganisms in soil was reduced to a certain degree, and the combination of the biochar and the phage φYSZPK for remediation has the most significant promotion effect on the functional diversity and stability of microorganisms in soil ($p<0.05$), indicating that the remediation technology has a significant effect on remediation of the spread of resistance bacteria, and is also favorable for maintaining and improving the ecological functional diversity and stability of microorganisms in soil after remediation.

The technology for simultaneous control and inactivation of multiple resistance pathogenic bacteria and resistance genes in soil-vegetable systems by combination of the biochar and the phage therapy has the advantages of high broad spectrum, low ecological risk and environmental friendliness, and is a compound pathogenic bacterium contaminated soil remediation technology with good application prospects.

What is claimed is:

1. A method of using a polyvalent phage φYSZPK for controlling and inactivating antibiotic resistant pathogenic bacteria in a soil-vegetable system, wherein the polyvalent phage is active against both *Pseudomonas aeruginosa* and *Klebsiella*, and wherein the polyvalent phage φYSZPK is mixed with a biochar.

2. The method of claim 1, wherein the biochar is produced by burning wheat straw as a raw material at a high temperature of 450° C., and with basic physical and chemical properties being total carbon: 548.4 g/kg, total nitrogen: 13.4 g/kg, C/N: 33.6, ash content: 175.5 g/kg, total phosphorus: 2.1 g/kg, total potassium: 10.3 g/kg, and pH: 8.5.

3. The method of claim 1, wherein the polyvalent phage φYSZPK and the biochar are mixed in a mass ratio of 1:1000, and wherein the mixture of the polyvalent phage φYSZPK and the biochar is applied to a contaminated soil.

4. The method of claim 1, wherein the polyvalent phage φYSZPK is used for preparing a product for control and inactivation of antibiotic resistant pathogenic bacteria in a soil-vegetable system.

5. The method of claim 4, wherein the product for control and inactivation of antibiotic resistant pathogenic bacteria in a soil-vegetable system, comprises the polyvalent phage φYSZPK and a biochar.

6. The method of claim 5, wherein the product comprises a mixture of the polyvalent phage φYSZPK and the biochar in a mass ratio of 1:1000, and wherein the product is applied to a contaminated soil.

* * * * *